(12) United States Patent
Rosengart

(10) Patent No.: US 7,066,953 B2
(45) Date of Patent: Jun. 27, 2006

(54) METHOD AND APPARATUS FOR PERFORMING AN ANASTAMOSIS

(76) Inventor: Todd K. Rosengart, 1016 Brittany Rd., Highland Park, IL (US) 60035-3952

( * ) Notice: Subject to any disclaimer, the term of this patent is extended or adjusted under 35 U.S.C. 154(b) by 379 days.

(21) Appl. No.: 10/175,357

(22) Filed: Jun. 19, 2002

(65) Prior Publication Data

US 2003/0074007 A1 Apr. 17, 2003

Related U.S. Application Data

(63) Continuation-in-part of application No. 10/060,958, filed on Jan. 30, 2002, now Pat. No. 6,814,751.

(60) Provisional application No. 60/328,731, filed on Oct. 12, 2001.

(51) Int. Cl.
*A61F 2/06* (2006.01)

(52) U.S. Cl. ................................................. 623/1.23

(58) Field of Classification Search ............... 623/1.23, 623/1.11; 606/108
See application file for complete search history.

(56) References Cited

U.S. PATENT DOCUMENTS

| | | |
|---|---|---|
| 3,946,503 A | 3/1976 | Buchan et al. |
| 5,456,712 A | 10/1995 | Maginot |
| 5,484,565 A | 1/1996 | Larsen et al. |
| 5,522,882 A | 6/1996 | Gaterud et al. |
| 5,549,553 A | 8/1996 | Ressemann et al. |
| 5,554,139 A | 9/1996 | Okajima |
| 5,575,771 A | 11/1996 | Walinsky |
| 5,662,614 A | 9/1997 | Edoga |
| 5,662,675 A | 9/1997 | Polanskyj Stockert et al. |
| 5,702,412 A | 12/1997 | Popov et al. |
| 5,718,683 A | 2/1998 | Ressemann et al. |
| 5,799,282 A | 8/1998 | Rakshit et al. |
| 5,823,948 A | 10/1998 | Ross, Jr. et al. |
| 5,830,178 A | 11/1998 | Jones et al. |
| 5,843,028 A | 12/1998 | Weaver et al. |
| 5,944,019 A | 8/1999 | Knudson et al. |
| 5,957,940 A | 9/1999 | Tanner et al. |
| 5,976,107 A | 11/1999 | Mertens et al. |
| 5,976,178 A | 11/1999 | Goldsteen et al. |
| 5,980,484 A | 11/1999 | Ressemann et al. |
| 5,999,909 A | 12/1999 | Rakshit et al. |
| 6,001,068 A | 12/1999 | Uchino et al. |
| 6,014,630 A | 1/2000 | Jeacock et al. |
| 6,024,748 A | 2/2000 | Manzo et al. |
| 6,026,814 A | 2/2000 | LaFontaine et al. |
| 6,027,519 A | 2/2000 | Stanford |
| 6,030,413 A | 2/2000 | Lazarus |
| 6,033,378 A | 3/2000 | Lundquist et al. |
| 6,036,682 A | 3/2000 | Lange et al. |
| 6,056,719 A | 5/2000 | Mickley |

(Continued)

FOREIGN PATENT DOCUMENTS

GB 579266 7/1946

(Continued)

OTHER PUBLICATIONS

International Search Report for PCT/US02/32726.

*Primary Examiner*—David O. Reip
(74) *Attorney, Agent, or Firm*—Kilyk & Bowersox, P.L.L.C.

(57) ABSTRACT

Graft delivery systems and methods for performing a cardiac by-pass procedure using a graft or a mammary artery are described. A combination of catheters and guide devices through the aorta, coronary artery, and the thoracic region can be used to accomplish these procedures.

54 Claims, 12 Drawing Sheets

U.S. PATENT DOCUMENTS

| | | |
|---|---|---|
| 6,063,114 A | 5/2000 | Nash et al. |
| 6,068,637 A | 5/2000 | Popov et al. |
| 6,074,416 A | 6/2000 | Berg et al. |
| 6,083,234 A | 7/2000 | Nicholas et al. |
| 6,120,432 A | 9/2000 | Sullivan et al. |
| 6,146,339 A | 11/2000 | Biagtan et al. |
| 6,146,355 A | 11/2000 | Biggs |
| 6,149,440 A | 11/2000 | Clark et al. |
| 6,157,852 A | 12/2000 | Selmon et al. |
| 6,162,246 A | 12/2000 | Barone |
| 6,165,139 A | 12/2000 | Damadian |
| 6,165,140 A | 12/2000 | Ferrera |
| 6,171,112 B1 | 1/2001 | Clark et al. |
| 6,186,942 B1 | 2/2001 | Sullivan et al. |
| 6,196,230 B1 | 3/2001 | Hall et al. |
| 6,206,849 B1 | 3/2001 | Martin et al. |
| 6,206,912 B1 | 3/2001 | Goldstein et al. |
| 6,210,312 B1 | 4/2001 | Nagy |
| 6,214,016 B1 | 4/2001 | Williams et al. |
| 6,224,585 B1 | 5/2001 | Pfeiffer |
| 6,241,667 B1 | 6/2001 | Vetter et al. |
| 6,253,769 B1 | 7/2001 | LaFontaine et al. |
| 6,340,441 B1 | 1/2002 | Meyer et al. |
| 6,508,252 B1 * | 1/2003 | Berg et al. .................. 128/898 |
| 6,511,491 B1 * | 1/2003 | Grudem et al. ............. 606/153 |
| 2001/0003985 A1 | 6/2001 | LaFontaine et al. |
| 2002/0108621 A1 | 8/2002 | Berg et al. |

FOREIGN PATENT DOCUMENTS

| | | |
|---|---|---|
| WO | WO 00/20064 | 4/2000 |
| WO | WO 00/24449 | 5/2000 |
| WO | WO 00/27312 | 5/2000 |

* cited by examiner

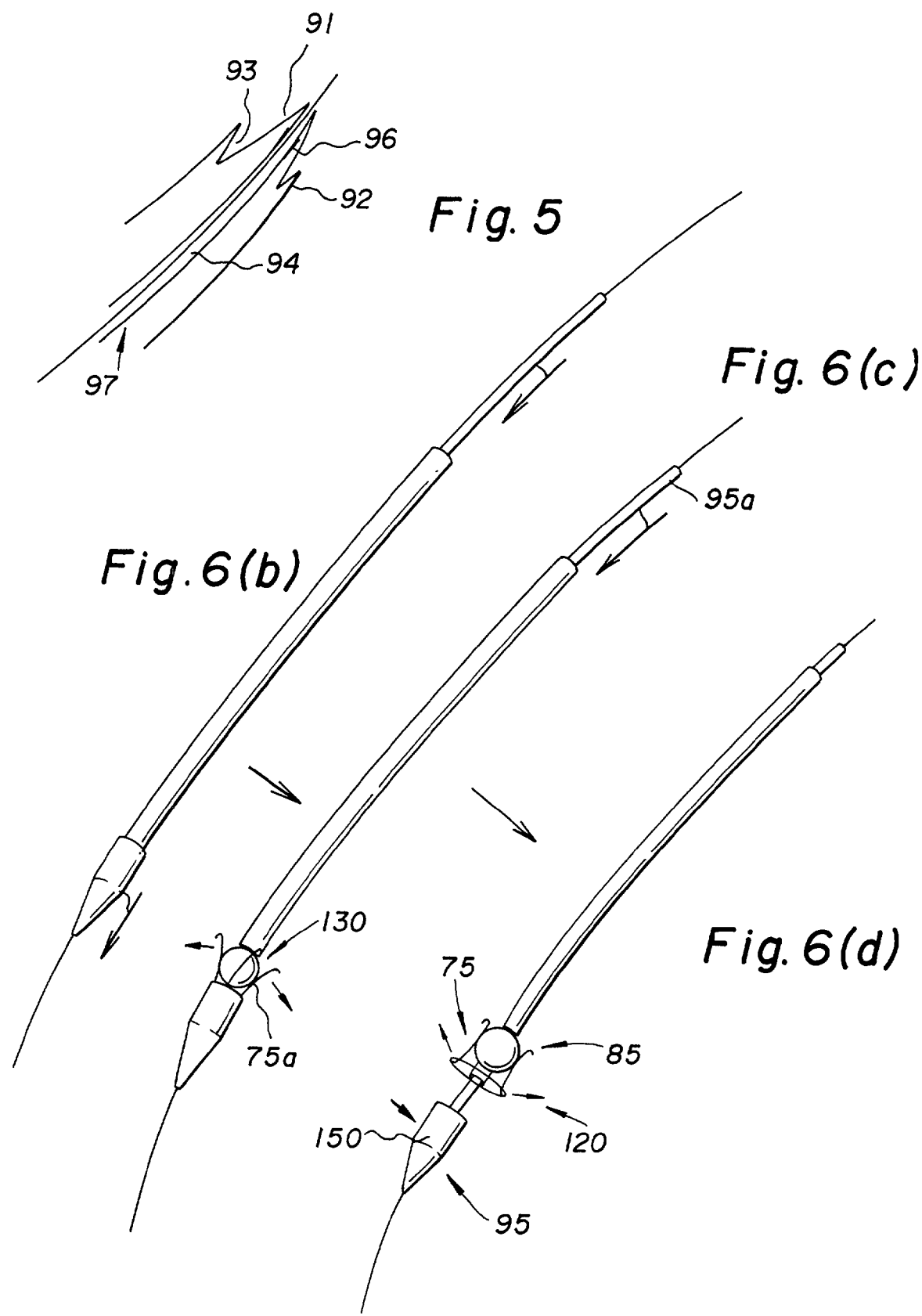

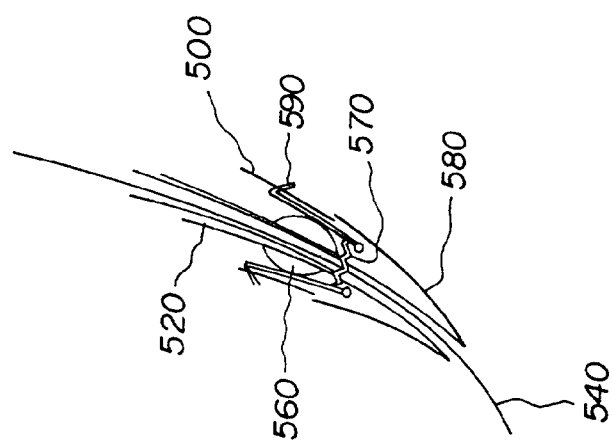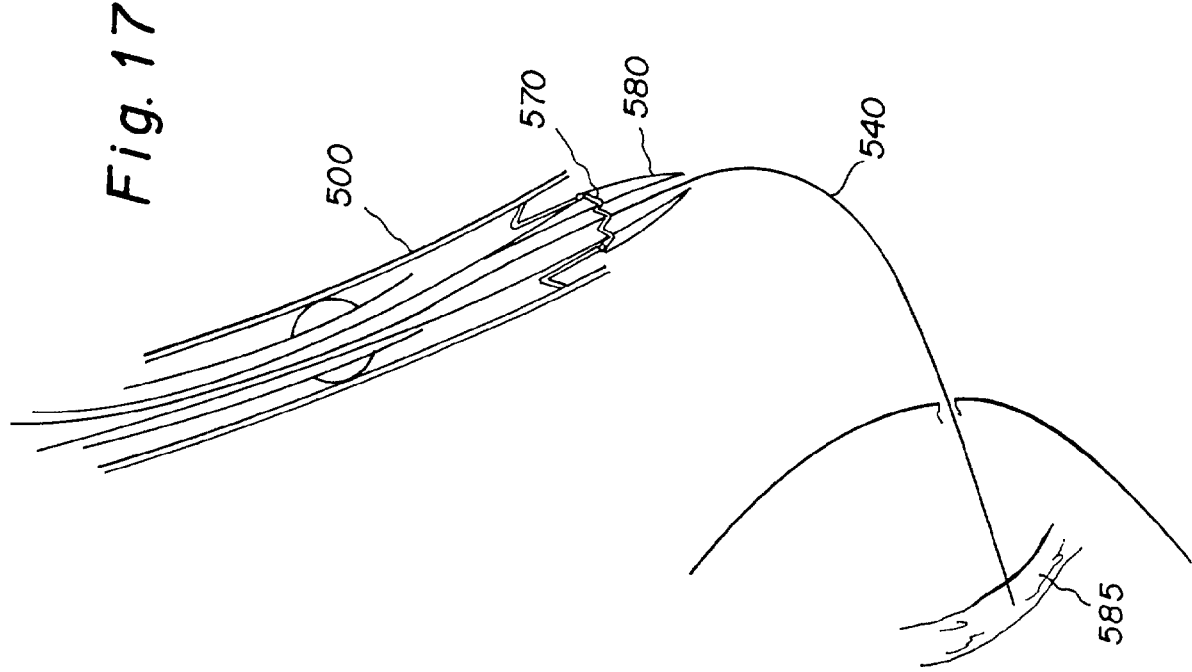

METHOD AND APPARATUS FOR PERFORMING AN ANASTAMOSIS

This application is a continuation in part of U.S. patent application Ser. No. 10/060,958, filed on Jan. 30, 2002, now U.S. Pat. No. 6,814,751, and also claims the benefit under 35 U.S.C. §119(e) of prior U.S. Provisional Patent Application No. 60/328,731 filed Oct. 12, 2001, and both are incorporated in their entirety by reference herein.

BACKGROUND OF PRESENT INVENTION

The present invention relates to an apparatus and a method for performing a cardiac by-pass procedure, also referred to herein as an anastamosis. This invention further relates to grafts for use in the repair, replacement, or supplement of a medical patient's natural body organ structures or tissues. The present invention also relates to methods and apparatus for delivering a graft to an operative site in a patient and for installing the graft at that site.

Several procedures are known for revascularizing the human heart in order to treat a patient with one or more occluded coronary arteries. One of the earliest of these procedures involves exposing the heart by a midline sternotomy. Following surgical exposure of the heart, the patient's aorta and vena cava are connected to a heart/lung machine to sustain vital functions during the procedure. The beating of the heart is stopped to facilitate performance of the procedure. Typically, a suitable blood vessel, such as a length of the patient's saphenous (leg) vein, is harvested for use as a graft. The graft is used to create a new, uninterrupted channel between a blood source, such as the aorta, and the occluded coronary artery or arteries downstream from the arterial occlusion or occlusions. A variation of the above procedure involves relocating a mammary artery of the patient to a coronary artery. Although the above-described sternotomy procedures grow more successful each year, the invasiveness of these procedures, the stopping of the heart, and the necessity for general anesthesia are significant disadvantages. Indeed, these disadvantages preclude the use of sternotomy procedures on many patients.

More recently, less invasive procedures have been developed for revascularizing the heart without using the heart/lung machine ("beating heart" procedures). Two problems with "beating heart" coronary artery repair are the active movement of the beating heart and the challenge of creating anastamoses to the aorta and coronary arteries while they are filled with blood. Various devices and methods have been devised to attempt to immobilize the heart and create a bloodless field to facilitate such beating heart procedures. Drugs may be administered to the patient to slow the heart during the procedure, stabilizing devices may be placed on the surface of the heart, and shunts or snares may be introduced into or around the coronary arteries to allow stabilization of the coronary arteries and construction of the coronary anastamoses in a bloodless field.

A less invasive method for revascularizing the human heart involves gaining access to the thoracic cavity by making incisions between the patient's ribs. This procedure is known as a thoracotomy. A thoracotomy procedure is substantially less traumatic than a midline sternotomy, but it is still too traumatic for some patients. An even less invasive procedure is known as thoracostomy, which involves the surgical creation of ports in the patient's chest to obtain access to the thoracic cavity. Specially designed instruments can be inserted through the ports to allow the surgeon to revascularize the heart without causing more significant trauma from a midline sternotomy. Thoracostomy bypass procedures are less traumatic than sternotomy bypass procedures, but the introduction of stabilization devices through thorocostomy ports is cumbersome, impractical, and of limited utility. Furthermore, bypasses to the coronary arteries that are located on dependent portions of the heart are not readily possible with this technique.

Several patents have recently been filed or issued in the field of graft and stent assemblies and methods for use thereof. Of particular interest are the following U.S. Pat. Nos. 5,702,412; 5,944,019; 5,976,178; 6,026,814; 6,063,114; 6,068,637; 6,074,416; 6,120,432; 6,186,942; 6,196,230; 6,206,912; 6,253,769; 5,456,712; 5,522,882; and U.S. patent application Ser. No. 2001-0003985 A1. All patents, applications, and publications mentioned here and throughout the application are incorporated in their entirety by reference herein and form a part of the present application.

Accordingly, there is a need for a new improved method and apparatus for performing an anastamosis.

SUMMARY OF PRESENT INVENTION

The present invention relates to a graft delivery system, which includes a first elongated instrument that is insertable from the exterior of a patient's thoracic region into the patient through a thoracic aperture. The first elongated instrument preferably includes an aortic guide device, and is preferably an aortic guide wire. The aortic guide device is preferably capable of protruding inside the aorta or a branch vessel of the aorta at a predetermined location.

The present invention also includes a second elongated instrument that is insertable into the patient's vascular system. The second elongated instrument preferably includes a coronary catheter and a coronary guide device that is capable of navigating the coronary catheter to a coronary artery of the patient at a predetermined location. In the preferred embodiment, the coronary guide device is a coronary guide wire.

The present invention also includes a retrieving device, capable of retrieving the aortic guide device and the coronary guide device. Preferably, the retrieving device is capable of extracting the aortic guide device from the aorta to outside of a peripheral artery and extracting the coronary guide device through the thoracic aperture in the patient.

Furthermore, the present invention includes a third elongated instrument that is insertable from the exterior of the patient's thoracic region into the patient through the thoracic aperture. This third elongated instrument is navigated by the coronary guide device. Preferably, the third elongated instrument is within a graft that is to be used, for instance, in the by-pass procedure. However, the graft can also be placed within the third elongated instrument.

Also, the present invention includes an aortic catheter capable of cutting an aperture in the aorta or its branches, and capable of navigating the proximal end of a graft to this aperture.

Also, the present invention relates to a method for installing a graft that includes (a) creating a thoracic aperture in the thoracic region of the patient; (b) inserting a first elongated instrument through the thoracic aperture into the patient's thoracic region; (c) navigating the first elongated instrument to a pre-determined location on the aorta or one of the major branches of the aorta of the patient; (d) protruding the aortic guide device from the thoracic region into the aorta, thereby creating an aortic aperture; (e) inserting a second elongated instrument into the patient's vascular system; (f) navigating the second elongated instrument to a pre-determined location in the coronary artery; (g) protruding the coronary guide device to the outside of the coronary artery, thereby creating a coronary aperture; (h) retrieving the aortic guide device and extracting the distal end of the aortic guide device with the retrieving device from the aorta to outside of the peripheral artery, and retrieving the coronary guide device and extracting the distal end of the coronary guide device with the retrieving device from the thoracic region of the patient to outside of the thoracic region of the patient; (i) inserting a third elongated instrument through the thoracic aperture, wherein the third elongated instrument is preferably within the graft, and the coronary guide device is threaded through the third elongated instrument to provide a navigation path for the third elongated instrument to the coronary aperture; (j) navigating the third elongated instrument with the graft to the coronary aperture; (k) attaching the distal end of the graft to the coronary aperture to make a fluid-tight connection; (l) passing an aortic catheter over the aortic guide device; (m) inserting the distal end of the aortic catheter into the proximal end of the graft and navigating the proximal end of the graft to the aortic aperture; and (n) attaching the proximal end of the graft to the aortic aperture to make a fluid-tight connection.

The present invention also relates to graft delivery systems and methods of installing a graft using a mammary artery or similar pathway.

It is to be understood that both the foregoing general description and the following detailed description are exemplary and explanatory only and are intended to provide further explanation of the present invention, as claimed.

BRIEF DESCRIPTION OF DRAWINGS

The foregoing features of this invention will be more readily understood by reference to the following detailed description, taken with reference to the accompanying drawings, in which:

FIG. 5 is a schematic diagram of the aortic catheter/cutting device;

FIGS. 6(b), (c), and (d) are schematic diagrams of a thoracic catheter including an expandable object, a conical-shaped device and a skirt-like sheath;

FIG. 17 is a schematic diagram illustrating one method of delivering a coupler attached to the severed end of the mammary artery to the coronary artery.

FIG. 18 is a schematic diagram illustrating the appendages of the coupler that are deployed and are piercing the mammary artery.

DETAILED DESCRIPTION OF PRESENT INVENTION

The present invention relates to a graft delivery system that includes a first elongated instrument that is insertable from the exterior of a patient's thoracic region into the patient through a thoracic aperture. The first elongated instrument preferably is or includes an aortic guide device. The aortic guide device is preferably an aortic guide wire. The aortic guide device is preferably capable of protruding inside of the aorta or the major branches of the aorta at a predetermined location. The present invention may also include a second elongated instrument that is insertable into the patient's vascular system. The second elongated instrument preferably includes a coronary catheter and a coronary guide device that is capable of navigating the coronary catheter to a coronary artery at a pre-determined location. In the preferred embodiment, the coronary guide device is a coronary guide wire. The aorta guide device and the coronary guide device can be generally of the same type of construction.

The present invention may also include a retrieving device that can be steerable and is capable of retrieving the aortic guide device and the coronary guide device. Preferably, the retrieving device is capable of extracting the aortic guide device from the aorta to outside of a peripheral artery and extracting the coronary guide device through the thoracic aperture in the patient. Furthermore, the present invention may include a third elongated instrument that is insertable from the exterior of the patient's thoracic region into the patient through the thoracic aperture. This third elongated instrument is preferably navigated by the coronary guide device. Preferably, the third elongated instrument is inserted in the graft or the graft can be inserted in the third elongated instrument to be used in the by-pass procedure. The third elongated instrument preferably includes or is a thoracic catheter that is insertable through a thoracic aperture.

In one example, the first elongated instrument or parts thereof, such as the aortic guide device, can be inserted through a thoracic aperture. An airtight seal around the thoracic aperture's entry can be used to facilitate continued normal ventilation of the patient. The thoracic aperture's entry is preferably only as large as necessary to accommodate the first and third elongated instrument. More preferably, the thoracic aperture entry can be approximately equal to the largest of the diameters of the first elongated instrument, the third elongated instrument, a fiber optic light/camera system, a docking device, one end of the aortic catheter, and/or one end of the coronary guide wire. In the present invention, the most preferred diameter of the thoracic aperture is from about 5 mm in diameter to about 10 mm in diameter, though other diameters can be used. The fiber optic light/camera system may also be inserted through a separate aperture.

Figure 1:
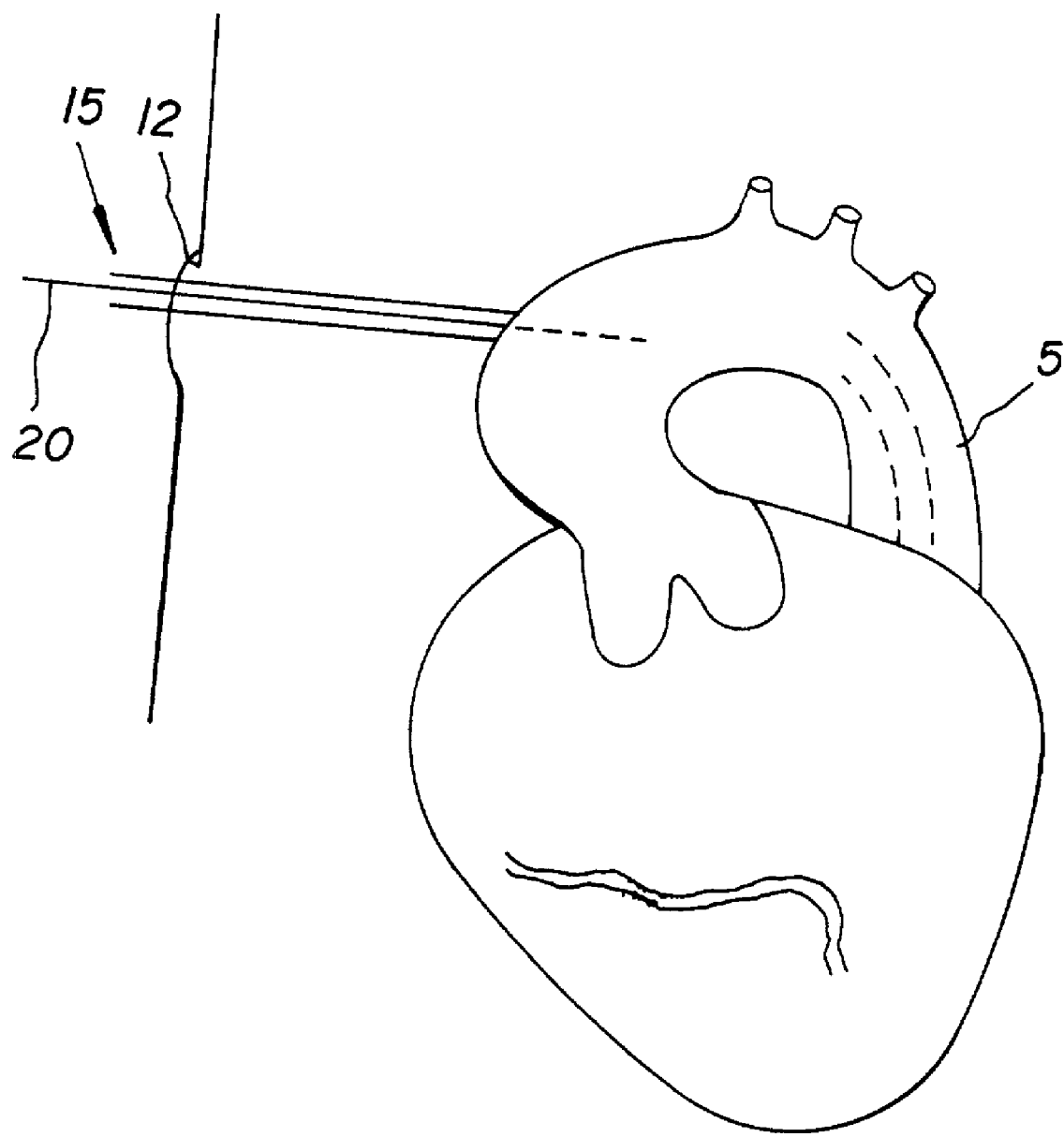
FIG. 1 is a schematic diagram showing the heart, the aorta, and the first elongated instrument having the aortic guide wire, of an embodiment of the present invention.

With reference to the figures, first elongated instrument 15 (FIG. 1), can be inserted from the exterior of the patient's thoracic region into a patient through thoracic aperture 12. First elongated instrument 15 may include aortic guide device 20 that can be advanced into and within the aorta or a major branch of the aorta at a desired position. In the preferred embodiment, aortic guide device 20 is an aortic guide wire that may be sharpened, stiffened or otherwise designed to facilitate aortic perforation. The sharp tip of the aortic guide device may be retractable or otherwise protected, or it may temporarily reside within the lumen of the first elongated instrument to prevent injury to extraneous tissues. The catheters and guide devices can be commercially available tools. The reference to "aortic" for aortic catheter is to better explain the location of use of the catheter and the size and shape requirements that would preferably be used in view of its location of use. This would be true to the other terms preceding "guide wire" and "catheter" and the like.

In the present invention, aortic guide device 20 can include a sharp end to perforate inside of aorta 5 and to protrude inside of aorta 5 or its branches. In the preferred embodiment, aortic guide device 20 is an aortic guide wire. First elongated instrument 15 may have a central lumen through which to pass aortic guide device 20 and may have a hollow distal chamber, similar to a pill-shaped form, which can occlusively be pushed or pulled up against the external wall of aorta 5 in the manner such that an aperture can be created in the wall of aorta 5 for entrance of aortic guide device 20. In the preferred embodiment of the present invention, aortic guide device 20 can also include a balloon at the end so that the retrieval device can capture the aortic guide device 26. The balloon can also prevent dislodgement once aortic guide device 20 enters the aorta. Preferably, as is described later, an aortic catheter, which can be passed over the aortic guide wire, can create an enlarged aortic aperture and be used to capture and navigate the proximal end of a free graft. The aortic catheter can include a sharp edge or rim at some distance proximal to a conical tip, such that the sharp edge can be made to cut out an aperture in the aorta of a diameter less than that needed for constructing the aortic anastamosis. The aortic catheter can also include a recess central to the cutting edge or rim to allow the aortic pledget to be captured, brought out and retrieved through the thoracic aperture or the peripheral artery. The location in which the aortic pledgets are brought out can depend on whether the aortic catheter is advanced over the aortic guide device from the peripheral artery or the thoracic aperture, respectively. The aortic catheter may also include a coaxially internal balloon catheter for capturing the proximal end of the bypass graft, as described below. The aortic catheter can be the first elongated instrument.

Figure 2:
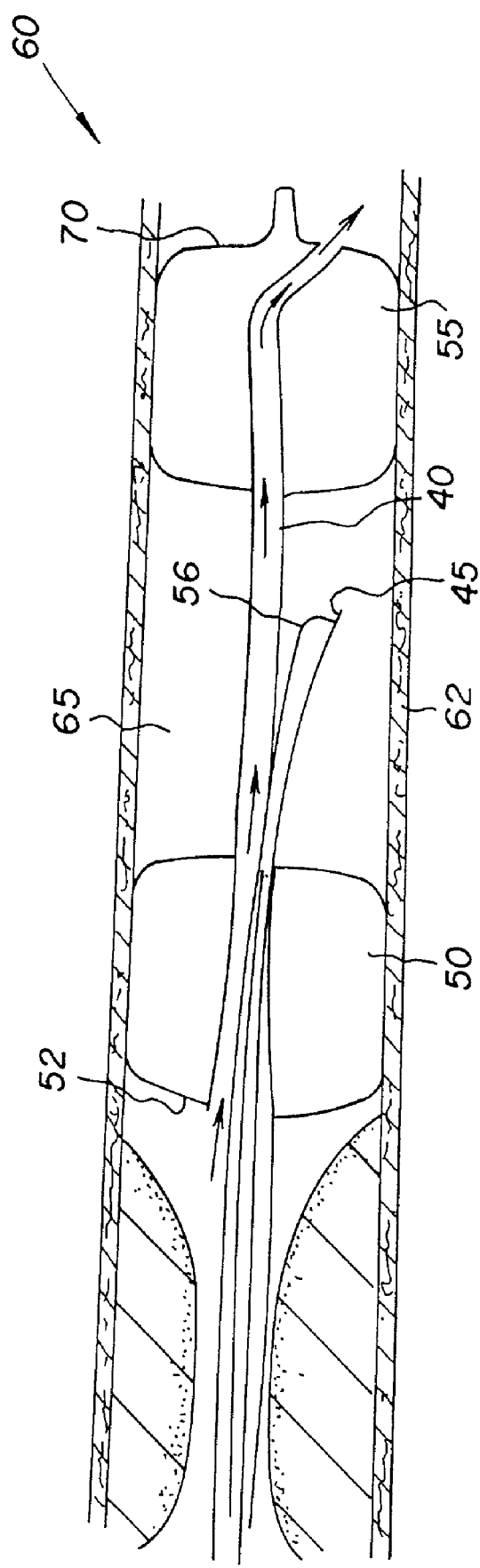
FIG. 2 is a cross-sectional schematic diagram of one embodiment of the second elongated instrument, which includes two expanding objects, a shaped perforating guide wire, and a flange.

The second elongated instrument that is insertable into the patient's vascular system includes a coronary catheter and a coronary guide device, an example of which is shown in FIG. 2. The coronary guide device, which is preferably a flexible coronary guide wire, is directed towards the coronary artery to preferably perforate the coronary artery at a predetermined location, and can protrude outside of the coronary artery. The coronary guide device may include at least one radio-opaque marker to determine its location within the coronary artery. The guide device, which may have a pre-shaped "J" or similar configuration, can perforate the coronary artery or be used to guide an aperture-creating device. The coronary catheter can be advanced over the coronary guide device or a conventional coronary guide wire. The coronary catheter can be appropriately positioned so that the coronary guide device can be advanced from within the catheter to expose the pre-shaped configuration and to allow a coronary perforation. A conventional guide wire used initially to position the coronary catheter can be withdrawn and be replaced by the perforating guide device. Alternatively, a guide wire can be replaced by a perforating guide device that may be directed toward the epicardial coronary wall by a flange or other similarly directing channel or component that is part of the coronary catheter. The second elongated instrument may optionally include at least one expandable object 50, FIG. 2, which can be a hemostatic object to block or restrict blood flow. Expandable object 50 is preferably a balloon. Expandable object 50 may include a first channel that prevents blood flow blockage by directing the blood flow from one side of the expandable object to the second side of the expandable object.

Figure 3A:
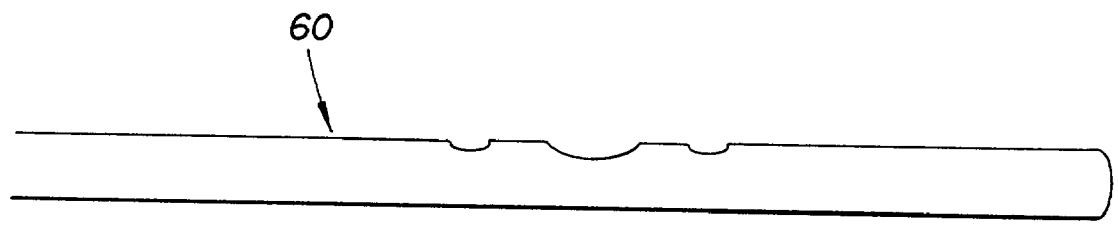
FIGS. 3(a), (b), and (c) are schematic diagrams showing one embodiment of the coronary perforating catheter.
Figure 3B:
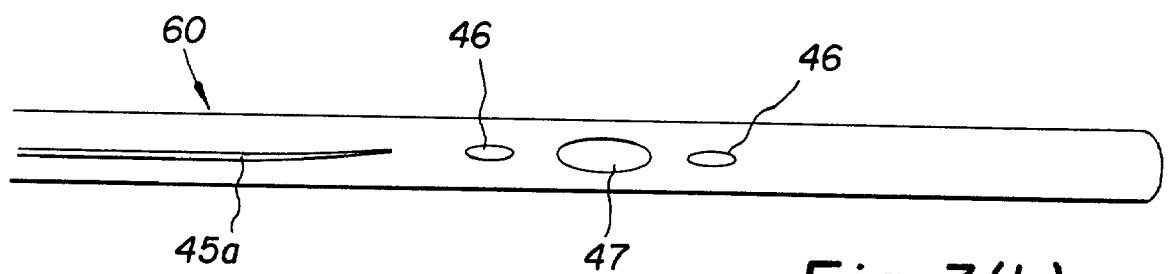
Figure 3C:
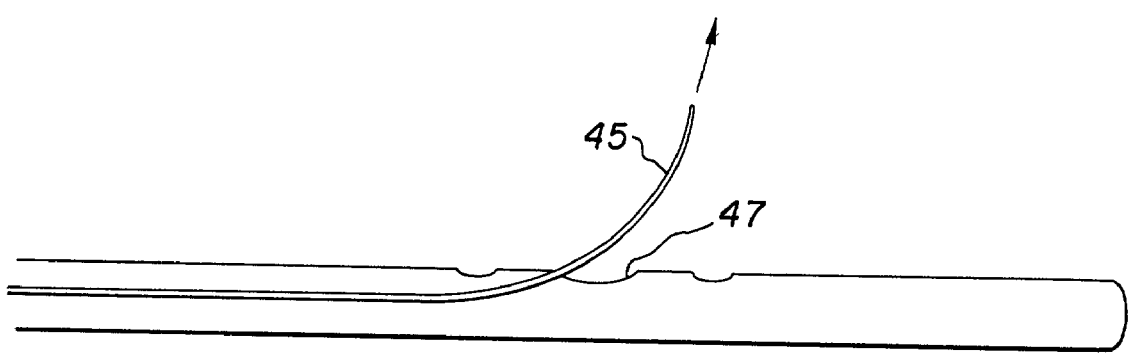

Expandable object 50 may include a perforating guide device, an example of which is shown in FIG. 2, as perforating guide device 45 in a second channel. In one example, perforating guide device 45 (FIGS. 2 and 3(a)–(c)) is preferably used to perforate coronary artery 62 at a predetermined location and can protrude outside of coronary artery 62. Preferably, the coronary guide device can be used to direct the second elongated instrument to coronary artery 62, or it may replace a conventional guide wire, for example guide wire 45a, FIG. 3. The coronary guide device and/or coronary catheter may include at least one radio-opaque marker 46, FIG. 3(b) to determine its location within the coronary artery. Perforating guide device 45 (FIGS. 2 and 3(a)–(c)) can be a T-shaped perforating guide wire. The preferred T-shaped perforating guide device ensures proper orientation of the thoracic catheter which subsequently passes over this device and can be aligned after the second channel is correctly oriented. This orientation of the second channel can in turn be determined by verifying the orientation of the appropriate radio-opaque markers on the coronary catheter or other appropriate markers. This orientation can be maintained to also ensure proper orientation of a dilator.

Perforating guide device 45 can be flexible, or may have a pre-formed shape, such as an "L" or "J" shape, with a sharp end to perforate the coronary artery. In the preferred embodiment of the present invention, second elongated instrument 60 may also include a 60–90 degree (or any angle) flange, such as flange 56 (FIG. 2) or flange 47 (FIGS. 3(b)–(c)) to direct T-shaped perforating guide device 45 towards the coronary artery wall to perforate the coronary artery.

Optionally, second elongated instrument 60 can also include second expandable object 55, which can be a hemostatic object positioned, with respect to the first expandable object 50, to form hemostatic chamber 65 within the coronary artery. First expandable object 50 and second expandable object 55 can include first channel 40 that extends between first expandable object 50 and second expandable object 55. In the preferred embodiment of the present invention, first expandable object 50 and second expandable object 55 are balloons. First channel 40 directs the blood flow from side 52 of first expandable object 50 blocking the blood flow to side 70 of second expandable object 55.

The coronary catheter or second elongated instrument can have two expandable objects 50 and 55, first channel 40, T-shaped perforating guide device 45 and 60 to 90 degree flange 56 at the end of T-shaped perforating guide device or a similarly shaped device. Preferably, the coronary guide device can be a T-shaped perforating device to ensure that the third elongated instrument, as will later be described, is properly oriented by using an adaptor on the third elongated instrument designed to receive T-shaped perforating guide device 45 to prevent undesired perforation of coronary artery 62 in an improper orientation.

Second elongated instrument 60 may advance over the coronary guide device 45*a*, FIG. 3(*b*), within the vascular system to a site, preferably within the distal coronary artery of adequate diameter with minimal atherosclerotic disease, and beyond the coronary occlusion or stenosis. Expandable objects 50 and 55 may be inflated to contact the inner side walls of the coronary artery and seal the blood flow. In this example, first channel 40 conducts coronary blood flow from side 52 of expandable object 50 to side 70 of expandable object 55. T-shaped perforating guide device 45 may then be advanced through the first or second channel and can be directed at a near-perpendicular angle by retractable or permanently positioned flange 56 such that T-shaped perforating guide wire 45 punctures the external coronary artery sidewall.

The retrieving device, which may be steerable, can advance into the aorta from the peripheral artery to receive, secure, and exteriorize the terminating end of the aortic guide device from the aorta or its branches to outside of the peripheral artery. Moreover, the same retrieving device can exteriorize the coronary guide device, or preferably the T-shaped perforating guide device, by advancing into the thoracic region of the patient and then may be passed through a pericardiotomy created by conventional methods to make contact with and secure to the terminating end of the coronary guide device. Furthermore, a retrieving device may include at least one aortic stabilizer to place and hold the instrument in a predetermined location. The retrieval device may include a retractable pin(s), a barb(s), a balloon(s), hook(s) or any combination thereof that are able to secure the terminating end of the guide devices, and/or bio-compatible adhesive or sealant that are able to achieve or provide temporary adhesion of the guide devices, or magnetically, electrically or otherwise attaching devices. In the preferred embodiment, the retrieving device and the end of the guide devices can be magnetized or be adapted to possess opposite polarities to improve the connecting ability of the two components.

Figures 4A, 4B, 4C:
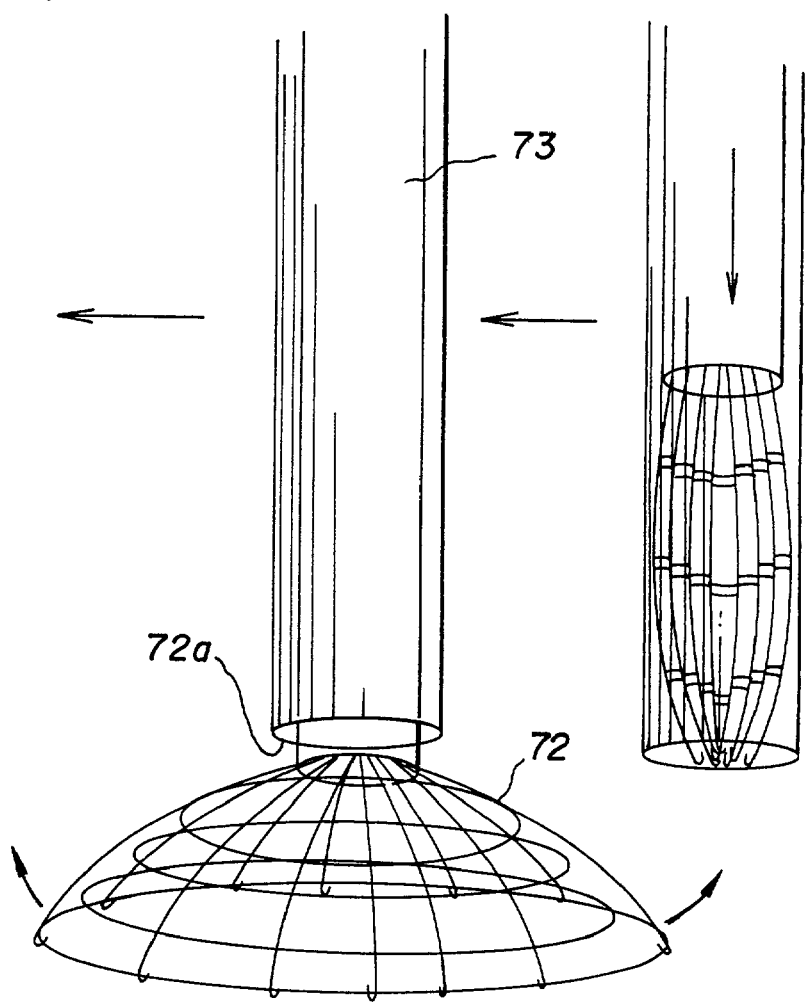
FIGS. 4(a), (b), and (c) are schematic diagrams of the retrieving device having a retractable cone-shaped hollow device.

For example, in FIGS. 4(*a*)–(*c*), a positively charged (magnetized) aortic guide device end is attracted to and can engage a negatively charged retrieving device 71, and a negatively charged aortic guide device end is attracted to and can engage a positively charged retrieving device 71. In the preferred embodiment, as illustrated in FIGS. 4(*a*)–(*c*), the end of retrieving device 71 is conical in shape to form a docking cone 72, with a wide opening at its end. In the example, as illustrated in FIGS. 4(*a*), (*b*), and (*c*), conical end 72 of retrieving device 71 can protrude out, as shown at FIG. 4(*b*), from the distal end of the retrieving device to create a large surface area. Conical end 72 can also be retreated, as shown in FIG. 4(*c*), back within retrieving device 71 to facilitate capturing the guide devices, especially if the guide devices are balloon-tipped. Therefore, the aortic guide device and the coronary guide device can readily contact and secure docking cone 72. Preferably, in this example, an aortic guide device passes along cylindrical wall 73 of retrieving device 71, which guides the aortic guide device as it is further inserted into and secured to the retrieving device. Preferably, the aortic guide device is passed through an apical aperture 72*a* in docking cone 72 and passed externally through the central channel of the retrieving device. Preferably, the magnetic material or other attracting devices may be localized at the apical aperture to maximally facilitate guide wire guidance. Additionally, when the balloon-tipped guide device contacts docking cone 72, the cone can be retreated, thereby securing the balloon-tipped guide device. The guide device and retrieving device 71 can then be withdrawn together. Once docking cone 72 secures the aortic guide device, retrieving device 71 can be withdrawn through the peripheral artery. In retrieving the coronary guide device, once docking cone 72 secures the coronary guide device, retrieving device 71 can be withdrawn through the thoracic aperture.

In the preferred embodiment, the guide devices are located under video and/or fluoroscopic guidance or other imaging devices. In the preferred embodiment, capture of the coronary or aortic guide device or preferably the T-shaped perforating guide device may be facilitated by inflation of a balloon near the terminus of this device, which serves to "suspend" and facilitate capture of the tip of the coronary or the aortic guide device or preferably the T-shaped perforating guide device within the pericardial space or aortic lumen.

Preferably, once the two ends of the aortic guide device are secured, an aortic catheter/cutting device can be passed over the guide device from the peripheral artery, through the aorta and out through the thoracic aperture to create an aortic aperture. Alternatively, the aortic catheter may be passed in the opposite direction. The aortic catheter/cutting device may consist of a dilator tip (e.g., dilator 91, FIG. 5), a cutting edge (e.g., cutting edge 92, FIG. 5) of lesser diameter than the diameter of the expanded coupler ring of the coupler device, a centrally situated shelf (e.g., shelf 93, FIG. 5) in which the cut aortic pledget can be retained, a central-most channel for passage of the aortic guide device (e.g., channel 94, FIG. 5), and a co-axially internal balloon (e.g., balloon 96, FIG. 5) (anastamosis) catheter (e.g., catheter 97, FIG. 5), which is expandable within the proximal graft coupler and is used to apply traction and guide the proximal end of the graft material.

Figure 6A:
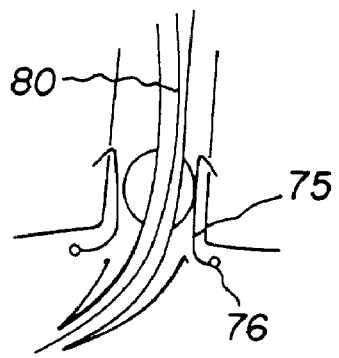
FIG. 6(a) is a schematic diagram of a thoracic catheter within the graft and a coupler attachable to the coronary artery and the graft.
Figure 7A:
FIGS. 7(a)–(c) are schematic diagrams of the coupler as compressed in the conical-shaped device and the coupler after its release from the conical-shaped device.
Figure 7B:
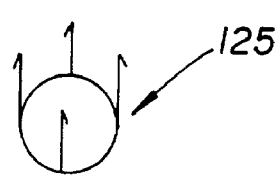
Figure 7C:
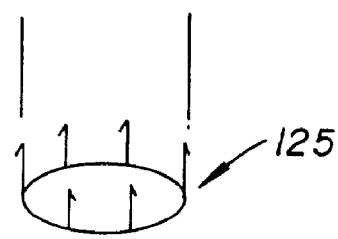

The third elongated instrument preferably is or includes thoracic catheter 80, FIG. 6 (a) and is inserted within the graft. A coupler is preferably placed on each end of the graft. This coupler can be at least one prong, at least one staple, at least one pin, at least one barb, or any combination thereof. One example of such a coupler is coupler 75. Coupler 75 may be deformable, may contain biocompatible sealants, and/or may include at least one sharp prong. In the preferred embodiment, for instance, the end 76 of coupler 75 attaching to the coronary artery and to the aorta expand to an external diameter of 5 to 10 mm. Other sizes can be used. More preferably, coupler 75 may include a ring of fine wire or other material that can be compressed in a spring-like manner. Ring 120 (FIGS. 7(*a*)–(*c*)) expands within the lumen and conforms to the internal geometry of the vessel upon its release from a conical-shaped device and is shown as 125, FIGS. 7(*b*) and (*c*). A conical-shaped device can be any device that preferably is hollow and can include reduced or tapered ends and that can enter into an artery or the aorta.

Figure 8:
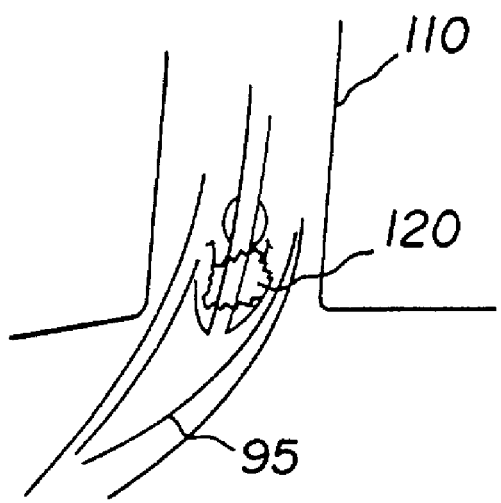
FIG. 8 is a schematic diagram of the thoracic catheter with the coupler positioned in the conical-shaped device.

In one embodiment of the present invention, the coupler at each end of the graft can be deformable, and preferably made of Nitinol or stainless steel, polyimide, other superelastic alloys, and the like. More preferably, the coupler at each end of the graft includes a ring that connects to the graft by means of arms made of distensible or flexible wire, such as flexible wire 75a, FIG. 6(c) or similar material to which are attached barbs or other means of penetrating the graft wall. Ring 120, FIG. 8, preferably within conical-shaped device 95, is located at each end of the graft 110. In the present invention, it is preferable to compress ring 120 into conical-shaped device 95 at the exterior of the patient's thoracic region. In one example, conical-shaped device 95 may be integrated into each end of graft 110 and a ring, fine wire or other material can be compressed in conical-shaped device 95. The distal conical device can be a component of the thoracic catheter, while the proximal conical device can be separate component.

Figure 9:
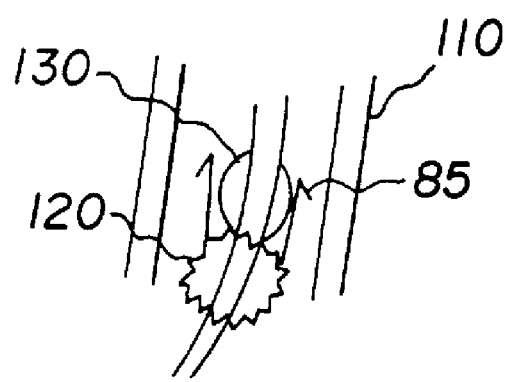
FIG. 9 is a schematic diagram of the position of the graft with respect to the sheath and the coupler.

Ring 120, FIG. 9, may connect to the graft by means of arms of distensible wire to which are attached sharp, downward-directed or otherwise barbed, flexible appendages as shown at 85, FIG. 9. The appendages may include prongs, staples, pins, metallic or plastic bars, or a combination thereof or may attach to the graft by at least one adhesive.

The graft material of the present invention is preferably a length of saphenous vein or mammary artery (IMA) on the exterior or the interior of the thoracic catheter. Other graft material can be used, such as artificial grafts and the like. Preferably, appendage 85 couples to graft 110 by expandable object 130 that can also act as a forcing instrument. Expandable object 130 may be a balloon, spring, or a combination thereof. More preferably, expandable object 130 is a balloon.

Figure 10:
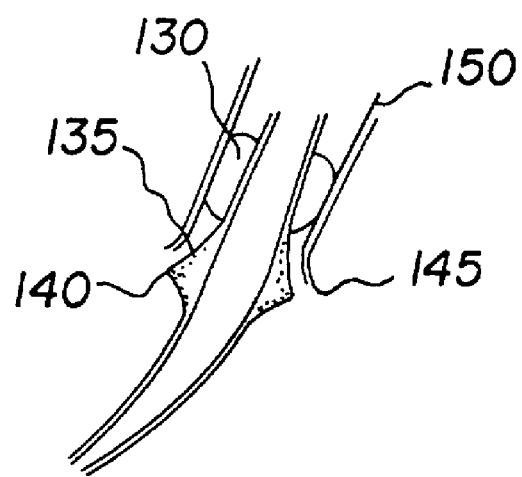
FIG. 10 is a schematic diagram of the concave curvature and the step-off of the third elongated instrument.

In the preferred embodiment of the present invention, the thoracic catheter of the third elongated instrument may include expandable object 130, FIGS. 6(c) and 10, conical-shaped device 95, which can be advanced by an internal component of the thoracic catheter, such as internal component 95 (FIG. 6(c)). From the conical-shaped device, a skirt-like sheath, such as skirt-like sheath 150 (FIG. 6(d)), can extend to cover appendages 85. A concave curvature, such as concave curvature 135 (FIG. 10), everts the graft edge, such as graft edges 145, outwards. A step-off, such as step-off 140, limits the advancement of the catheter and the attached graft to the exterior of the anastamotic site. The sheath and/or the conical device can also exist as a separate component.

Figure 11:
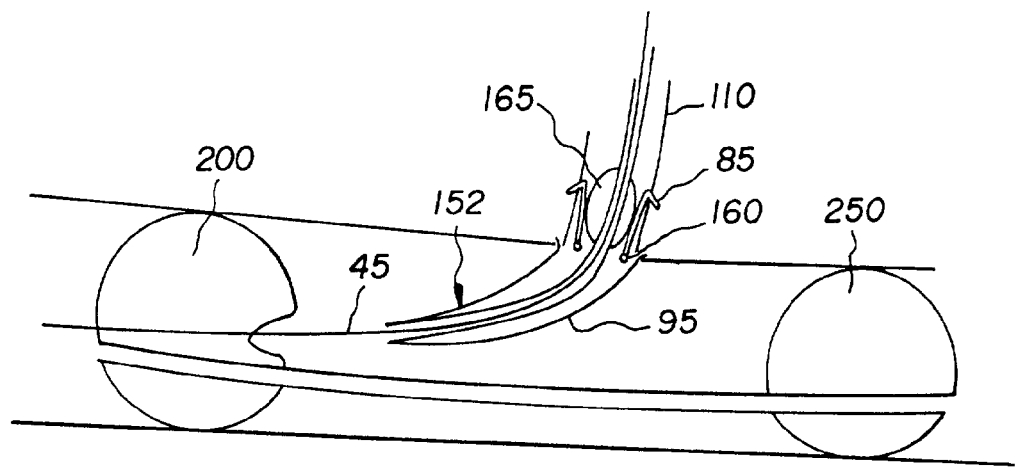
FIG. 11 is a schematic diagram of the conical-shaped device within the lumen of the coronary artery and the two expandable objects of the second elongated instrument.

Enlarging instrument 152, FIG. 11, is preferably located at the distal end of graft 110, and more preferably at the distal end of conical-shaped device 95. In the most preferred embodiment, enlarging instrument 152 is located at the end of conical-shaped device 95, wherein conical-shaped device 95 includes a 90 degree or other angle. However, enlarging instrument 152 can be located anywhere so long as it is capable of creating a circular arteriotomy into which conical-shaped device 95 can be inserted. In one embodiment of the present invention, enlarging instrument 152 can be a dilator or a cutter, and the dilator may be passed over the coronary or aortic guide device prior to passage of the thoracic catheter and graft.

Optionally as shown in FIG. 11, dilator/cutter 152 may open tissue external to the coronary artery or aorta to exceed the external diameter of the graft material so that this extraneous tissue does not impinge on the anastomosis. The edge of dilator/cutter 152 may be beveled to form a sharp edge. Dilator 152 can be adapted to have a groove or a receiving site for the T-shaped perforating guiding device to assure proper orientation of the dilator/cutter. The advancement of the dilator/cutter may be limited by expandable object 200, which can be a hemostatic object, acting as a "stopper" or by the dimensions of the dilator or the diameter of a step-off in the dilator.

In one example, dilator/cutter 152 can be tapered so that the coronary or aortic aperture is substantially less than the external diameter of graft 110. Dilator 152 may be configured with a tapered circular tip expanding to a diameter of approximately 3 mm at a distance equal to approximately one-half the distance between expandable objects 200 and 250, such that a circular aperture is created in the coronary artery at a point halfway between expandable objects 200 and 250.

In the present invention, the coronary aperture is preferably of a pre-determined size created by the diameter of dilator 152. In an embodiment wherein a dilator is passed prior to passage of the thoracic catheter, the dilator can widen to dimensions, such as, but not limited to, approximately 8 mm long by 5 mm wide for a distance of approximately 1 cm beyond its 3 mm diameter coronary aperture point so that epicardial fat or overlying muscle can be effectively cleared from a position overlying the coronary, thereby avoiding the potentially deleterious incorporation of these tissues in the coronary anastamosis. The size of the dilator/cutter can vary based on the diameter of the target artery and/or the planned cross-sectional area of the anastamotic device.

An aortic dilator, which can be incorporated into the tip of the aortic catheter, may be circular or have other configurations and can be from about 2 mm to about 8 mm, such that the size of the aperture created is smaller than that of the graft and the expanded aortic anastamotic mechanism. This aperture, as with the coronary aperture, may be post-dilated with larger dilators after completion of the anastamosis to accommodate the size of the graft.

Marker 160 (FIG. 11), which is preferably a radio-opaque marker, can be placed within graft 110 to detect the position of graft 110. Expandable object 165, which can be a hemostatic object, can be the forcing instrument that attaches appendage 85 of the coupler to graft 110, or appendage 85 may passively fix to the graft after removal or advancement of the sheath. Furthermore, the third elongated instrument, which is preferably a thoracic catheter, may include a fiber optic light/camera system. However, the light/camera system may also be in a separate elongated instrument.

The apparatus discussed above can also be used for performing an anastamosis using a mammary artery. The preferred method of performing anastamosis using a mammary artery is described later.

In a preferred method of the present invention, the first elongated instrument can be inserted into the aorta or one of the aortic branches from the thoracic aperture. The first elongated instrument can include an aortic catheter and an aortic guide device. Alternatively, the aortic catheter can pass over the aortic guide device as a separate component. The aortic guide device, with or without the aortic catheter, may be capable of creating an aperture through the aorta wall. Essentially, the aortic guide device can be used to navigate to the desired location of the aorta wall and pierce through the aorta wall. Alternatively, one of the major branches of the aorta may be accessed in an analogous fashion. The aortic guide device can be used to initiate the aperture at a desired location in the aortic wall. The creation of the aperture can be done, for instance, by mechanical means or light energy means. The aperture permits the first elongated instrument and/or the aortic guide device to protrude through the aperture. The first elongated instrument and/or the aortic guide device can be introduced through the thoracic aperture and one end can be extracted through a peripheral artery, preferably through a conventional sheath or introducer through the femoral artery located in the leg of the patient.

Figure 12A:
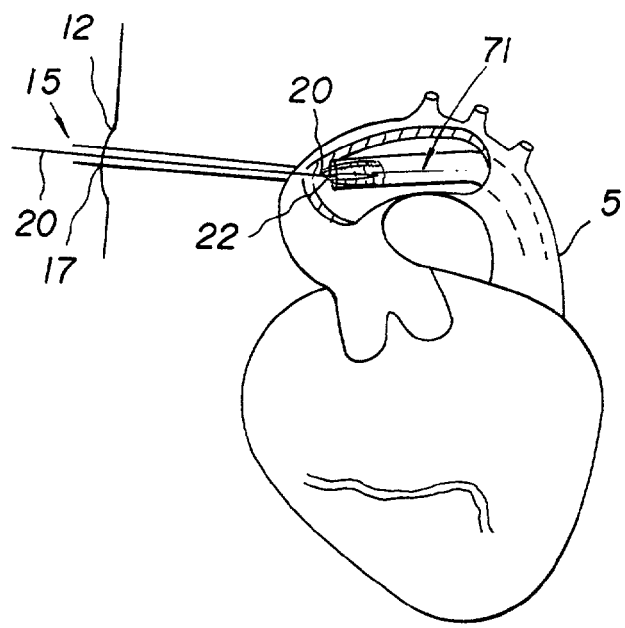
FIGS. 12(a)–(c) illustrate one method of capturing/receiving the aortic guide device.
Figure 12B:
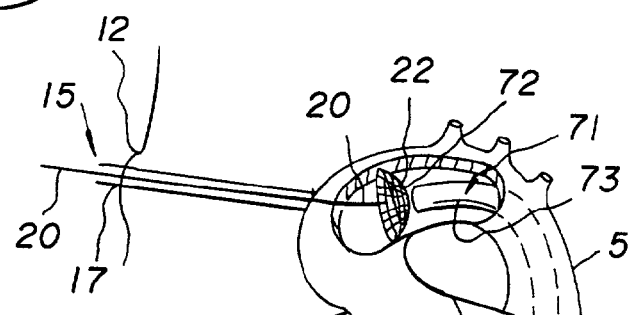
Figure 12C:
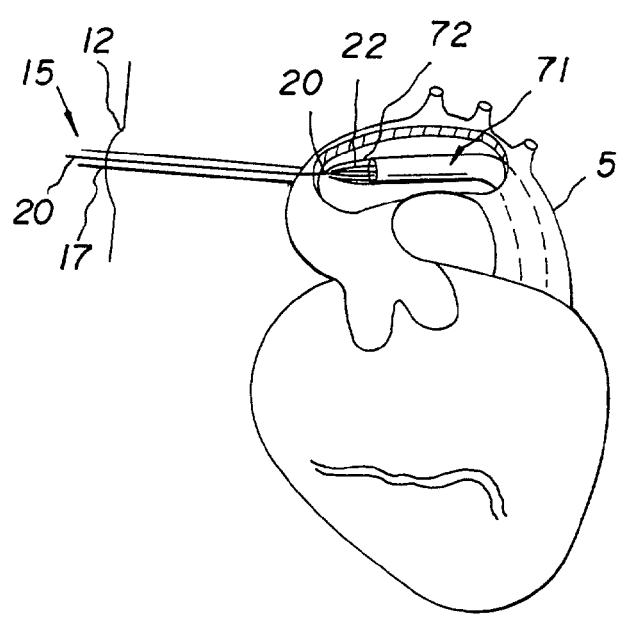

The method of extracting one end of the aortic guide device from the aorta through a peripheral artery includes inserting a retrieving device into a peripheral artery and navigating the retrieving device to the aorta, preferably at approximately the insertion point of the aortic guide device, which is protruding into the aorta. Preferably, the insertion point and/or the retrieval point may be in the descending aorta. Preferably, the retrieving device is magnetized to easily grasp the aortic guide device. FIG. 12(a) illustrates an example of retrieving device 71 navigated at approximately the insertion point of aortic guide device 20 having a balloon 22. Once the retrieving device reaches its predetermined location, the cone-shaped end of the retrieving device is exposed so that the aortic guide device easily contacts the retrieving device. For example, as illustrated in FIG. 12(b), cone-shaped end 72 is exposed and aortic guide device 20 having a balloon-tip is in contact with retrieving device 71. The cone-shaped or otherwise tapered end can then be closed, thus securing the guide device, as illustrated in FIG. 12(c). Once the aorta guide device is secured, both the aortic guide device and the retrieving device can be navigated to the outside of the patient through a peripheral artery, or the guide device may be exteriorized by passing it through a central channel of the retrieving device.

Figure 13:
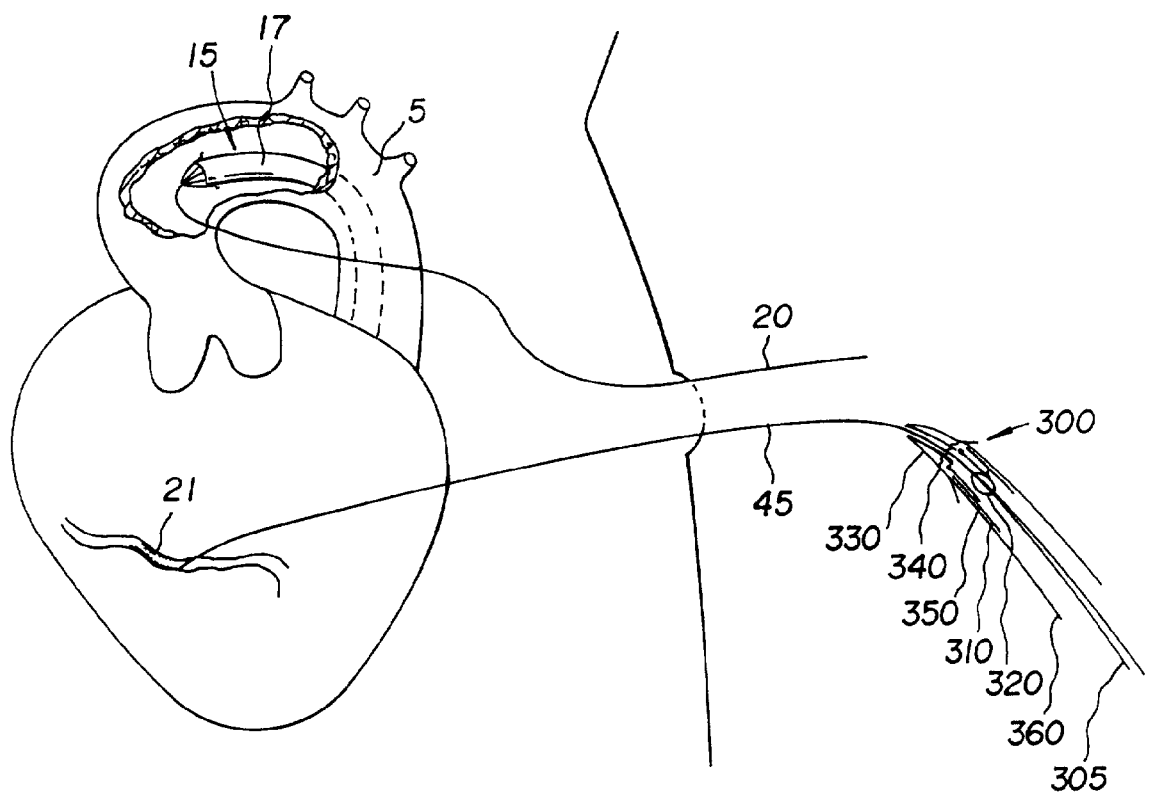
FIG. 13 is a schematic diagram illustrating the approach of the third elongated instrument with the coupler and the conical-shaped device towards the coronary artery.

The second elongated instrument (e.g., the coronary catheter with coronary guide device) can be introduced through the femoral artery of a patient and along the aortic passage. This second elongated instrument may pass the location of the aperture created by first elongated instrument 15 and/or aortic guide device 20 and further passes through any existing blockage, e.g. blockage 21 (FIG. 13). Once past blockage 21 (in other words, below the blockage), the coronary guide device, or more preferably, T-shaped perforating guide device 45 (FIG. 13), can be used to create an aperture below the blockage. In the preferred embodiment, T-shaped perforating guide wire 45 protrudes through the coronary artery.

Upon the creation of the coronary aperture, the retrieving device, that can be steerable, is introduced through the aperture in the thoracic region of the patient. This device retrieves the coronary guide device, which is protruding through the coronary aperture, in a similar manner as it can retrieve the aortic guide device. The retrieving device can retrieve the guide devices by mechanical methods, magnetic methods, or other attachment methods that are capable of grabbing or otherwise securing the guide devices at each aperture location. For instance, the device with the necessary retrieving means can go and retrieve the coronary guide device (or T-shaped perforating guide device 45 (FIG. 13)) protruding from the coronary aperture. The retrieving device then preferably navigates the coronary guide device through a pericardial aperture and to the outside of the patient through the aperture created in the thoracic region. Thus, preferably one end of each guide device and/or the aortic catheter is located outside the chest wall of the patient and the other end of each guide device and/or the aortic catheter is located outside of the patient through a peripheral artery.

A sheath, a coupler and a conical-shaped device to which the sheath may be attached are preferably at each end of graft 360, FIG. 13 (proximal end and distal end). Additionally, the third elongated instrument, e.g., thoracic catheter 305 (FIG. 13) preferably with expandable object 320, which can act as a hemostatic object, are placed into graft 360. In one example, elongated instrument 300 (FIG. 13) illustrates coupler 340 and conical-shaped device 330 with attached sheath 310 at the end of graft 360 closer to the coronary artery. As demonstrated, the conical-shaped device can be attached to an inner element of the thoracic catheter, and the sheath can exist as an extension of the conical shaped device. The sheath and/or the conical-shaped device can be separate from the thoracic catheter.

In a preferred embodiment, sheath 310 prevents appendage 350 of coupler 340 to penetrate graft 360 during loading. Coupler 340 can be attached onto graft 360 preferably at the end of graft 360 by means of the appendages 85 (FIG. 11). In a preferred embodiment, the proximal coupler is placed, followed by placement of the distal coupler and the thoracic catheter. Coupler 340, while it can have any design, preferably has a following design as described below.

The attachment of coupler 340 (FIG. 13) onto graft 360 can be done by any conventional means such as barbs, or can be sewed onto the graft, or can be attached with adhesives. The ring is preferably attached to the graft by locking barbs that are tension-loaded such that the barbs release upon tension being removed. Tension is removed by way of withdrawing a retaining sheath, such that the barbs are deployed into the graft wall. The sheath may exist separately from the thoracic catheter, or may extend as a skirt from the conical device. The sheath may be withdrawn or otherwise moved to uncover the appendages prior to or after advancement of the graft onto the guiding devices. The ring of the preferred embodiment is compressed and can be placed in a conical-shaped or other shaped device such as conical-shaped device 330. Conical-shaped device 330 may also include an aperture through the tip of the cone that permits the insertion of a guide device. The guide device is preferably threaded through the conical-shaped device and the inner diameter of the graft to provide a navigation path for the graft to the site of the coronary aperture.

The third elongated instrument, preferably with expandable object 320, is preferably used to stabilize the movement of graft 360 relative to the coronary aperture site. Additionally, as will later be described, the third elongated instrument with preferably the expandable object permits the releasing of the flexible ring from the conical-shaped device, which further releases the attached barbs or other connecting means onto the wall surrounding the coronary aperture site.

With the conical-shaped device and the ring properly positioned at the end of the graft, a sheath can be withdrawn. Preferably, in one example, sheath 150 (FIG. 6(d)) can be withdrawn by advancing an inner element 95a (FIG. 6(c)) of the thoracic catheter to which the conical-shaped device 95 and sheath 150 are attached, while holding coupler 75 in place by means of the expanded expandable device. Advancement of the sheath exposes appendage 85 of coupler 95. The expandable object 320 can then be further expanded, driving the barbs or other attachment means of appendage 350 through graft 360 (FIG. 13). Additionally, the process of driving the barbs can also occur due to passive expansion of these barbs. In one embodiment, an external collar against which the barbs can be driven is added and can serve as additional hemostatic or biologic functions.

The proximal connector can be attached in a similar fashion, either before or after positioning the distal connector. Preferably, the sheath is separate from the conical device and/or the thoracic catheter, and may be withdrawn by direct manipulation. The coupler appendages may deploy passively when the sheath is withdrawn, or may be driven into the graft wall by a balloon inflation. The proximal conical-shaped device, which preferably includes an apical aperture for passage of the guide devices, may also be separate from the thoracic catheter, and can be removed by manipulation of the aortic balloon catheter as described below.

A preferred loading sequence may occur as follows: 1) the proximal coupler contained by a sheath and a conical device is placed in the proximal end of a graft, 2) the proximal coupler appendages are released by withdrawing the sheath while maintaining the position of the coupler within the graft with a balloon inflated within the coupler or by other means, thereby securing the position of the proximal coupler relative to the graft, 3) the third elongated instrument, containing the distal coupler constrained by the sheath and/or the conical device, is loaded through the distal end of the graft and through the aperture in the proximal conical device, 4) the distal coupler appendages are deployed by advancing the internal element of the thoracic catheter, thereby securing the position of the distal coupler relative to the graft.

Once the distal, and preferably, the proximal couplers are attached to the graft, the graft containing the thoracic catheter is advanced over the coronary guide device, and potentially through the pericardial aperture, and the conical-shaped device is then inserted into the coronary aperture, preferably to a point where the conical-shaped device passes entirely through the coronary aperture. This is preferably accomplished by a dilator at the end of conical-shaped device 330. At this point, the expandable object or balloon in the interior of the graft remains inflated so that the expandable object or balloon still presses against the coupler and the graft. An inner-most element of the third elongated instrument, which distally is attached to the conical-shaped device, can then be pushed forward while the coupler is held in place by holding the expandable object in position (the inner-most element of the third elongated instrument can slide relative to the component of the third elongated instrument to which the expandable object is attached). This pushing movement of the conical-shaped device releases the compressed ring from the conical-shaped device. The releasing of the compressed ring thus permits the now uncompressed ring, with one end attached to the graft, to press against the entire circumference around the coronary aperture. This action further releases and imbeds any attachment means, such as barbs, into the interior wall of the coronary artery surrounding the coronary aperture, and creates a fluid-tight connection by transferring the tension exerted by the expanded ring through the distensible arms to the appendages. A bio-adhesive or other sealing agents can be used to further ensure a fluid-tight connection between the graft and the walls surrounding the coronary aperture. In a preferred embodiment, the creation of the aperture by the dilator, located at the distal end of conical-shaped device, and deployment of the coupler is nearly a continuous process, obviating the need for expandable objects in the coronary artery.

At this point, the conical-shaped device, which is preferably collapsible and flexible, can be withdrawn from the coronary artery through the graft and to the exterior of the patient by way of the thoracic aperture. This would also be true for the collapsible expandable object, and the third elongated instrument.

The aorta cutting catheter, which can be a dilator/cutter at the end of the aortic catheter, can be passed from the femoral or other peripheral artery over the aortic guide wire through the aorta, cutting or dilating an aperture in the aorta, and out through the thoracic aperture. The cut aortic pledget can be extracted as the cutting catheter is passed out the thoracic aperture over the aortic guide device. The cutting catheter can be fixed to the guide device to facilitate traction as it passes through and cuts the aortic wall by way of a restraining node on the guide device or by other ways. After creating the aortic aperture, but prior to constructing the aortic anastamosis, the aortic catheter resides in the aortic aperture in a hemostatic manner. The aortic catheter can be passed from the thoracic aperture through the aortic wall or one of the branches of the aorta and out the peripheral artery. An aortic balloon catheter can reside coaxially within an external aortic cutting catheter, or the aortic catheter can possess a distal balloon.

Once the distal end of the aortic catheter is appropriately positioned, preferably outside of the thoracic aperture, the aortic guide device can be removed and the distal end of the coronary guide device or the T-shaped perforating guide device can then be inserted into the aortic catheter, which can have a balloon at its end, and the coronary guide device can be fed completely through to the femoral artery or other entry point of the patient such that the distal end of the coronary guide device or the T-shaped perforating guide device is visible at this location. In one alternative preferred embodiment, if the length of the graft is long enough to be visible or to be physically outside of the thoracic aperture, the aorta catheter, preferably with a balloon, can be inserted into the unattached end of the graft without the need to feed the coronary guide device or T-shaped perforating guide device into the aorta catheter. This would be a more simplified approach if it is physically possible due to the length of the graft. Either approach can be used depending upon the circumstances and the length of the graft.

The aortic catheter with balloon is inserted into the proximal (unattached) end of graft such that the balloon engages the coupler at the proximal end of the graft to navigate the proximal end of the graft to the aortic aperture site. As indicated above, the use of the coronary guide wire or the T-shaped perforating guide device, with the feeding of this device into the aortic catheter, is for the purpose of guiding the aorta catheter preferably with a balloon into the unattached (proximal) end of the graft. Thus, the coronary guide device or the T-shaped perforating guide device makes it quite possible to navigate the aortic catheter with the balloon into the proximal end of the graft. Upon reaching the site, the aortic catheter with the balloon is withdrawn towards the aortic aperture to a point where the end of the graft is prepared for attachment onto the wall surrounding the aortic aperture. A coupler, such as described earlier, is used at this end of the graft 360 (FIG. 14) to attach onto the aorta in a similar manner as the coupler that was used to attach the distal end of the graft that is now attached to the coronary artery. In other words, a compressed tension loaded ring has been previously attached onto the proximal end of the graft and a device similar to the conical-shaped device is preferably used to keep the releasable ring in a compressed state.

Figure 14:
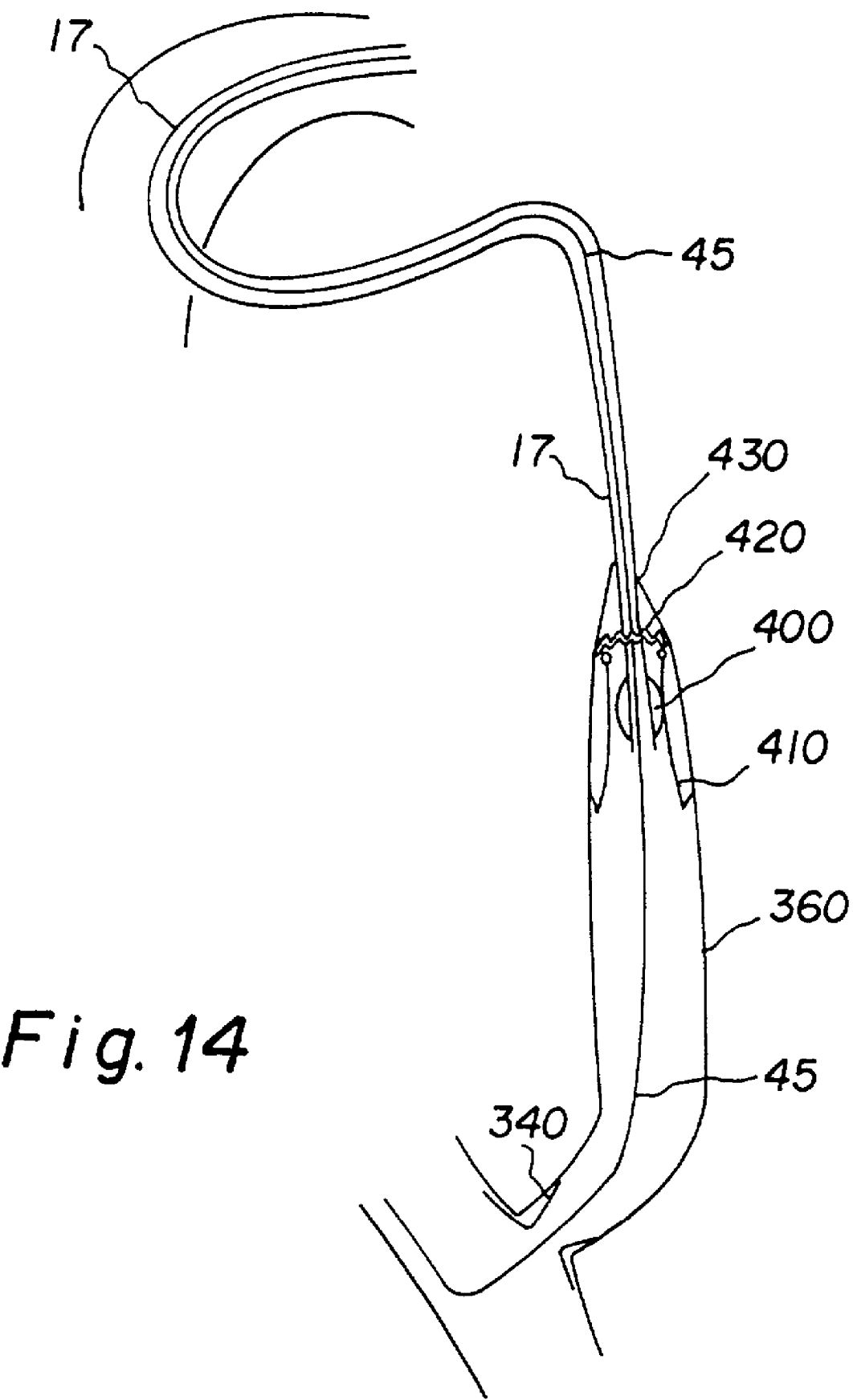
FIG. 14 is a schematic diagram illustrating one method of maneuvering the proximal end of the graft towards the aorta.

The aortic catheter with the balloon is preferably inserted through the aperture of the second conical-shaped device. Once the conical-shaped device is holding the compressed ring, the balloon can be expanded to press against the graft and/or coupler, which permits the ability to maneuver and navigate the graft to the aortic aperture. FIG. 14 illustrates an example wherein catheter 17 with balloon 400 is inserted through aperture 430. Additionally, compressed ring 420 is inside the conical-shaped device and balloon 400 is expanded to press against graft 360 and/or coupler 410. Once at the aperture site, and after traction with the balloon on the coupler has caused the conical-shaped device to enter through the aortic aperture, the balloon can be deflated slightly in order to avoid pressing against the graft wall while having a sufficient diameter to press up against the conical-shaped device and to remove the conical-shaped device from the compressed ring. This procedure permits the ring to release to its normal diameter and attach onto the wall surrounding the aortic aperture, thereby attaching the proximal end of the graft onto the aorta wall in a manner analogous to the distal connection. The aortic catheter with balloon and the conical-shaped device can then be retrieved from this area by retracting the coronary guide device (if used) or preferably T-shaped perforating guide device 45 (if used) and aortic catheter with balloon along with the collapsed conical device through the original entry point of the femoral artery at the leg site. Again, bio-adhesive or other sealing means can be used to further ensure a fluid-tight connection between the graft and the wall surrounding the aortic aperture.

With respect to a bypass conducted on the mammary artery, in this procedure, a thoracic aperture can be created in order to obtain access to the desired mammary artery to be used for the bypass procedure. Then, using conventional surgery techniques, one end of the mammary artery can be cut (using, for instance, a thoracoscope) in order to create a distal end or severed end of the mammary artery. This end of the mammary artery can then be prepared for attachment onto the coronary aperture.

With respect to the bypass procedure using a mammary artery, once the mammary artery is severed to create a severed end of the mammary artery, the mammary guide device is navigated from the thoracic aperture to a point where the mammary guide device enters into the severed end of the mammary artery and is preferably exited outside of a peripheral artery to the point where it is visible. The mammary guide device can be captured and be exited outside of a peripheral artery in the same way as described above with respect to capturing and exiting the aortic guide device using the retrieving device. Alternatively, the mammary guide device can be passed from the peripheral artery through the mammary artery wall or through the severed end of the mammary artery and be retrieved in a manner analogous to that for the coronary guide device. A thoracic catheter can then be inserted along the mammary guide device such that the distal end of the thoracic catheter exits the thoracic aperture and the proximal end exits from the peripheral artery. At this point, the mammary guide device can be withdrawn from the patient.

Also, the coronary guide device can then be navigated such that the distal end of the coronary guide device exits out the thoracic aperture as well. At this point, the distal end of the coronary guide device and the distal end of the thoracic catheter are visible. The distal end of the coronary guide device can be fed through the end of the thoracic catheter such that it also exits out of the peripheral artery.

Preferably, the distal end of the thoracic catheter has an expandable device or an inflatable balloon. The expandable device is preferably positioned at or near the location where the mammary artery will be severed. Preferably, the mammary artery can be severed at any time before guiding the mammary artery to the coronary artery aperture. The expandable device can be inflated such that it presses up against the walls of the mammary artery and thus the mammary artery, by way of the thoracic catheter, can be guided along the coronary guide wire to the coronary aperture. In a preferred embodiment, just as in the above-described bypass procedure, the coronary guide device is fed through a conical-shaped device which holds a compressible coupler that is or will be attached to the severed end of the mammary artery. The coronary guide device, once inserted into and through the coupler, preferably through the conical-shaped device, which also includes inserting through the thoracic catheter, actually exits out of the peripheral artery. The thoracic catheter carrying the coupler and the sheath can be positioned, for example, by visually or otherwise detectable marks on the sheath, such that the appendages of the coupler can be deployed in a manner analogous to the distal coupler deployment described above.

The thoracic catheter, along with the severed end of the mammary artery, can then be guided to the coronary artery aperture and coupled to the coronary aperture in the same manner as described above using the same release procedure described. Afterwards, the various catheters and guide devices can be withdrawn from the original insertion points of the patient.

Thus, the procedure remains the same wherein a mammary guide wire is introduced like the coronary guide device or like the first elongated instrument discussed earlier, from the thoracic aperture, through the mammary artery and exited through the peripheral artery by the retrieving device and, after positioning of a thoracic catheter with a coupler mechanism over the mammary guide wire, the mammary guide wire is removed and the coronary guide device is fed through the end of the thoracic catheter and is used to guide the cut end of the mammary artery to the coronary aperture. The coronary guide device or second elongated instrument is the same as described previously and is introduced in the same way and creates a coronary aperture in the same way as discussed above.

A thoracic catheter is fed through the mammary artery, in an antegrade or retrograde fashion, to the point where the thoracic catheter, preferably with a balloon, a coupler, a sheath and a conical device, is fed through the cut end of the mammary artery such that it enters into the interior of the cut mammary artery to an extent such that the balloon with the thoracic catheter can be expanded in order to press up against the coupler, which can be attached to the distal end of the mammary artery via the deployed appendages, sufficiently to be able to navigate and direct the cut end of the mammary artery to the coronary aperture site. Once at the coronary aperture site, the same coupling as described above and the same procedure used to release the conical-shaped device or other releasing mechanism used with respect to the coronary aperture can be used here as well. After releasing the attachment means, such as the ring, in order to create a fluid tight connection at the coronary aperture, the thoracic catheter, preferably with a balloon, can be withdrawn from the original entry point of the patient as well as the coronary guide device.

For example, and in more detail, at least one aperture of from about 1 to about 7 millimeters in diameter can be created to dissect the mammary artery away from the chest wall and cut one end of the mammary artery in order to create a severed end or distal end of the mammary artery. Preferably, an endoscopic camera is used to help with this procedure. The distal end of the retained mammary artery can be ligated, and the proximal end can be controlled with a clip or a clamp or other means. The mammary guide device and/or first elongated instrument, which is preferably the mammary catheter, can be inserted into the mammary artery from the thoracic region or from the peripheral artery prior to or following transection. At this point, preferably the expandable object is inflated to stop any blood flow. The mammary guide device then is captured by the retrieving device and exited through a peripheral artery. A second elongated instrument, which can be similar to the second elongated instrument discussed previously, passes through any existing blockage. The coronary guide device can be flexible or may have a pre-formed shape, such as an "L" or "J" shape, with a sharp end to preferably protrude through the coronary artery. The coronary guide device, which can protrude through the coronary aperture into the pericardial space and the mammary guide device, are retrieved by a retrieving device as previously discussed above.

Once the mammary guide device and the coronary guide device are preferably extracted outside of the patient through the peripheral artery and the thoracic aperture, the mammary guide device can be used to deliver a third elongated instrument to the distal end of the mammary artery in an antegrade or retrograde fashion. The third elongated instrument is preferably the thoracic catheter. In the preferred embodiment, the coupler is placed at the end of the thoracic catheter. Preferably, the coupler is a compressible ring that is placed inside the conical-shaped device and/or the sheath at the end of the catheter. The thoracic catheter is preferably used to deliver the coupler to the distal end (severed end) of the mammary artery. However, the coupler within the conical-shaped device can also be delivered by mammary artery catheter from inside the patient's vascular system. Once properly positioned by visual markers on the outside of the sheath or by other means, the sheath can be advanced relative to the coupler and the appendages can be deployed, as previously described.

The procedure for delivering the distal end of the mammary artery to the coronary artery and attaching the mammary artery to the coronary artery are similar to the previously discussed procedure for delivering and attaching the distal end of the graft to the coronary. More specifically, a thoracic catheter containing the coupler and the conical-shaped device (analogous to the thoracic catheter for use with the saphenous graft) can be passed through the mammary catheter and/or over the mammary guide device in a manner analogous to loading of the distal end of the vein graft. The mammary guide wire can then be removed. The coronary guide wire is then passed through the central lumen of the conical shaped device and the thoracic catheter as previously described. The thoracic catheter can then be positioned fluoroscopically or visually at the distal, transected end of the mammary artery, as previously described, the inflated thoracic catheter balloon can hold the coupler in position, and the sheath and/or conical-shaped device can then be advanced, allowing deployment of the graft appendages. The mammary coupler can then be deployed over the coronary guide device as for the saphenous vein distal anastomosis.

Figure 15:
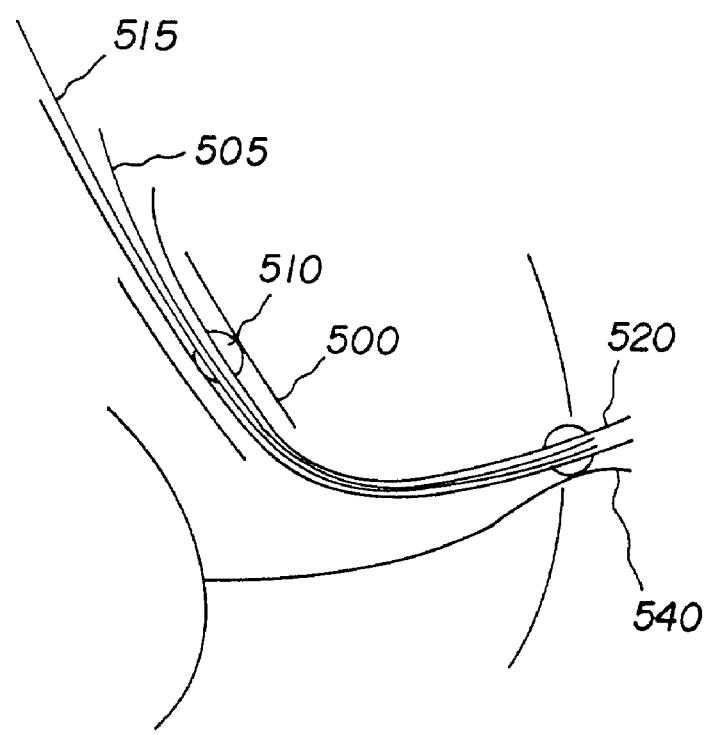
FIG. 15 is a schematic diagram showing the severed mammary artery, the mammary guide wire and the coronary guide wire protruding outside of the patient's thoracic region and the mammary catheter inserted inside the mammary artery.

In one example as shown in FIG. 15, once mammary artery 500 is severed to create a severed end of the mammary artery, mammary guide device 515 is navigated to a point where mammary guide device 515 exits into the severed end of mammary artery 500 and is preferably exited outside of a peripheral artery, by a retrieving device, to the point where it is visible. In the preferred embodiment, mammary catheter 505 also includes expandable objects 510 to prevent bleeding from the severed end of mammary artery 500. Once the ends of mammary guide device 515 are outside of the peripheral artery and the thoracic aperture, thoracic catheter 520 can be inserted along mammary guide device 515. Also, coronary guide device 540 can be navigated such that the distal end of coronary guide device 540 exits out of the thoracic aperture as well. At this point, the distal end of coronary guide device 540 and the end of thoracic catheter 520 out of the thoracic region of the patient are visible.

Figure 16:
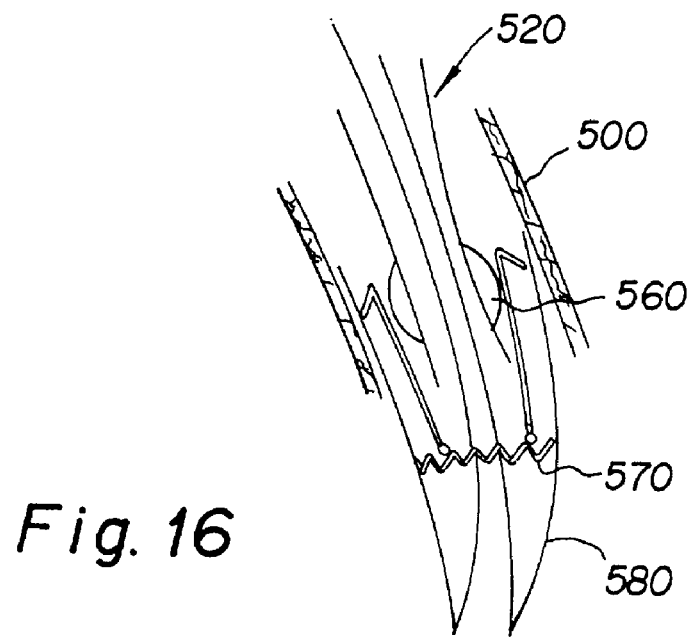
FIG. 16 is a detailed schematic diagram illustrating one example of the coupler and the conical-shaped device at the severed end of the mammary artery.

FIG. 16 illustrates an end of thoracic catheter 520, including expandable object 560 or an inflatable balloon, coupler 570, and conical-shaped device 580. Preferably, once thoracic catheter 520 is inserted into the severed end of mammary artery 500 and exits the peripheral artery and/or the thoracic aperture, the mammary guide device is removed.

In FIG. 17, coronary guide device 540 is fed through conical-shaped device 580 which holds coupler 570 that is attached to the severed end of mammary artery 500. Coronary guide device 540 guides coupler 570 and unattached end of mammary artery 500 to coronary artery 585. FIG. 18 illustrates appendages 590 that are deployed and are piercing mammary artery 500. Additionally, in FIG. 18, thoracic catheter 520 along with the severed end of mammary artery 500 are guided to the coronary artery aperture and coupled to the coronary aperture.

The following U.S. patents provide components that can be used in the systems, devices, and methods of the present invention and are incorporated in their entirety by reference herein and form a part of the present application: U.S. Pat. Nos. 6,206,849; 6,165,140; 6,165,139; 6,162,246; 6,157,852; 6,146,355; 6,146,339; 6,083,234; 6,056,719; 6,036,682; 6,340,441; 6,241,667; 6,224,585; 6,214,016; 6,210,312; 5,976,107; 5,957,940; 5,843,028; 5,830,178; 5,718,683; 5,662,675; 5,662,614; 5,575,771; 5,554,139; 5,549,553; 5,484,565; 6,033,378; 6,030,413; 6,027,519; 6,024,748; 6,001,068; and 5,980,484.

As can be seen by the various embodiments, there is preferably no interengaging of guide wires or instruments from each aperture site. In the current medical procedure, the wires or instruments from each aperture site are preferably not connected together or interengaged. The creation of the aortic aperture from the thoracic cavity is a simplified technique compared to a catheter based approach to creation of the aortic aperture from the vascular lumen. In addition, dilation of the coronary aperture and creation of the coronary anastomosis in a continuous approach eliminates the need for expandable objects on the coronary catheter, simplifying its design. In addition, creation of an expandable surface area on the retrieving device improves its efficiency. Finally, this technique is configured such that a guide device is always across a vascular aperture until an anastomosis is created, providing for the option of continuous hemostatic control by passage of a large diameter catheter over the guide wire, if needed.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims and equivalents thereof.

What is claimed:

1. A graft delivery system comprising:
   a first elongated instrument that is insertable from an exterior of a thoracic region of a patient into said patient, wherein said first elongated instrument comprises an aortic guide device, wherein said aortic guide device is capable of protruding inside of an aorta at a predetermined location;
   a second elongated instrument that is insertable into a vascular system of said patient, wherein said second elongated instrument comprises a coronary catheter and a coronary guide device capable of navigating said coronary catheter to a coronary artery at a pre-determined location and is capable of protruding outside of said coronary artery;

a retrieving device capable of retrieving said aortic guide device and said coronary guide device and extracting said aortic guide device from said aorta to outside of a peripheral artery and extracting said coronary guide device through a thoracic aperture in said patient; and
a third elongated instrument that is insertable from said exterior of said thoracic region of said patient into said patient and is capable of being navigated by said coronary guide device or said aortic guide device.

2. The graft delivery system of claim 1, wherein said first elongated instrument further comprises at least one stabilizer to place and hold said first elongated instrument in a pre-determined location.

3. The graft delivery system of claim 1, wherein said aortic guide device comprises a balloon, a shapened end, or a combination thereof.

4. The graft delivery system of claim 1, wherein said graft delivery system further comprises an aortic catheter, and wherein said aortic catheter is capable of navigating an end of a graft to an aortic aperture.

5. The graft delivery system of claim 4, wherein said aortic catheter further comprises a dilator or a cutter having a rim that is capable of capturing aortic pledgets.

6. The graft delivery system of claim 4, wherein said aortic catheter further comprises a coaxially internal catheter.

7. The graft delivery system of claim 1, wherein said coronary catheter comprises a perforating wire having a pre-shaped figure.

8. The graft delivery system of claim 1, further comprising a perforating guide device capable of perforating said coronary artery.

9. The graft delivery system of claim 1, wherein said second elongated instrument further comprises a flange to direct a perforating guide device towards a wall of said coronary artery to perforate said coronary artery.

10. The graft delivery system of claim 1, wherein said second elongated instrument further comprises at least a first expandable object capable of blocking blood flow.

11. The graft delivery system of claim 10, wherein said first expandable object comprises a first channel, wherein said first channel directs said blood flow from one side of said first expandable object blocking said blood flow to a second side of said first expandable object.

12. The graft delivery system of claim 10, wherein said second elongated instrument further comprises a second expandable object capable of being positioned with respect to said first expandable object to form a chamber within said coronary artery, and wherein said first and said second expandable objects comprise a first channel that extends between said first and said second expandable objects and is capable of directing said blood flow from one side of said first expandable object blocking said blood flow to a side of said second expandable object not facing said first expandable object.

13. The graft delivery system of claim 10, wherein said first expandable object comprises a second channel housing a perforating guide device.

14. The graft delivery system of claim 1, wherein one end of said retrieving device is magnetic or electrically charged having an opposite polarity than said aortic guide device and said coronary guide device.

15. The graft delivery system of claim 1, wherein said retrieving device comprises a cone-shaped hollow device and a body.

16. The graft delivery system of claim 15, wherein said cone-shaped hollow device is retractable.

17. The graft delivery system of claim 15, wherein said cone-shaped hollow device is magnetized.

18. The graft delivery system of claim 15, wherein said cone-shaped hollow device is in contact with said body, wherein said body comprises a hollow central channel to exteriorize said aortic guide device and said coronary guide device through said hollow central channel.

19. The graft delivery system of claim 15, wherein said cone-shaped hollow device is capable of capturing said aortic guide device and said coronary guide device.

20. The graft delivery system of claim 15, wherein said cone-shaped hollow device is retracted inside said body until reaching a predetermined location, and is capable of protruding out from said body at said predetermined location, to create a conical surface area.

21. The graft delivery system of claim 1, wherein said retrieving device is steerable.

22. The graft delivery system of claim 1, further comprising a coupler at one or both ends of a graft, and a conical-shaped device located at one end or both ends of said graft, wherein said coupler is located within said conical-shaped device.

23. The graft delivery system of claim 22, wherein, the conical-shaped device is collapsible.

24. The graft delivery system of claim 22, wherein said conical-shaped device further comprises an aperture to pass said aortic guide device or said coronary guide device.

25. The graft delivery system of claim 1, further comprising a sheath within a graft.

26. The graft delivery system of claim 25, wherein said sheath is advanced by an inner element of a thoracic catheter to expose at least one appendage of a coupler.

27. The graft delivery system of claim 1, wherein said third elongated instrument comprises a thoracic catheter.

28. The graft delivery system of claim 27, wherein said thoracic catheter further comprises an expandable object.

29. The graft delivery system of claim 27, wherein said thoracic catheter comprises a distal step-off and an everting curvature to position a graft to an anastamotic site.

30. The graft delivery system of claim 1, further comprising an enlarging instrument at one or both ends of a graft, wherein said enlarging instrument comprises at least one marker to detect position of said graft.

31. The graft delivery system of claim 1, further comprising a fiber optic light/video camera system.

32. The graft delivery system of claim 1, wherein said second elongated instrument further comprises at least one channel to guide said coronary catheter to a predetermined location and to direct a perforating device through a wall of said coronary artery.

33. The graft delivery system of claim 1, wherein one end of said retrieving device further comprises adhesive material, barbs, hooks, or combinations thereof.

34. The graft delivery system of claim 1, wherein said third elongated instrument comprises an inner element attached to a conical-shaped device and is capable of advancing said conical-shaped device.

35. The graft delivery system of claim 34, wherein said conical-shaped device further comprises a sheath.

36. The graft delivery system of claim 35, wherein said sheath is a separate entity than said conical-shaped device, and wherein said sheath is collapsible.

37. A method for installing a graft using said graft delivery system of claim 1 comprising:
a) creating a thoracic aperture in said thoracic region of said patient;

b) inserting said first elongated instrument through said thoracic aperture into said thoracic region of said patient;
c) navigating said first elongated instrument to a predetermined location of said aorta or aortic branches of said patient;
d) creating an aortic aperture with said aortic guide device or an aortic catheter;
e) inserting said second elongated instrument into said vascular system of said patient;
f) navigating said second elongated instrument to a predetermined location in said coronary artery;
g) creating a coronary aperture to outside of said coronary artery with said coronary guide device;
h) retrieving said aortic guide device and extracting said aortic guide device with a retrieving device from said aorta to outside of said peripheral artery; retrieving said coronary guide device and extracting said coronary guide device with a retrieving device from a pericardial space or said thoracic region of said patient to outside of said thoracic region of said patient, wherein said retrieving device for said aortic guide device and said coronary guide device are the same or different;
i) inserting said third elongated instrument through a thoracic aperture, wherein said third elongated instrument is within said graft, and said coronary guide device is threaded through said third elongated instrument to provide a navigation path for said third elongated instrument to said coronary aperture;
j) navigating said third elongated instrument with said graft to said coronary aperture;
k) attaching an end of said graft to said coronary aperture to make a fluid-tight connection;
l) passing an aortic catheter over said aortic guide device from said peripheral artery, through said aorta or an aortic branch, and out of said thoracic aperture;
m) inserting a distal end of said aortic catheter into the proximal end of said graft and navigating said proximal end of said graft to said aortic aperture; and
n) attaching said proximal end of said graft to said aortic aperture to make a fluid-tight connection.

38. The method of claim 37, further comprising a coupler attached to distal end of said graft and wherein said coupler is compressed within a conical-shaped device, said conical-shaped device is inserted through said coronary aperture, and wherein said coupler is released from within said conical-shaped device to attach said coronary artery to said graft, and said conical-shaped device is removed from said coronary artery.

39. The method of claim 37, wherein said aortic catheter further comprises a balloon at one end to hold said proximal end of said graft and wherein said aortic catheter and said balloon are extracted through said thoracic aperture and engage said proximal end of said graft.

40. The method of claim 37, further comprising a coupler attached to said proximal end of said graft and wherein said coupler is compressed within a conical-shaped device, said conical-shaped device is inserted through said aortic aperture, and wherein said coupler at said proximal end of said graft is released from within said conical-shaped device to attach said aorta to said proximal end of said graft.

41. The method of claim 37, further comprising removing from said coronary artery said third elongated instrument before inserting said distal end of said aortic catheter into proximal end of said graft.

42. The method of claim 37, wherein said coronary catheter is navigated to a predetermined location in said coronary artery by said coronary guide device.

43. The method of claim 37, wherein said retrieving device comprises a body and a cone-shaped hollow device, wherein said cone-shaped hollow device is magnetic, electrically charged, includes an adhesive surface, or combinations thereof to retrieve said aortic guide device and said coronary guide device.

44. The method of claim 43, wherein said cone-shaped hollow device is in contact with said body, wherein said body comprises a hollow central channel to exteriorize said aortic guide device and said coronary guide device through said hollow central channel.

45. The method of claim 43, wherein said cone-shaped hollow device is retractable.

46. The method of claim 43, wherein said cone-shaped hollow device is capable of capturing said aortic guide device by protruding outside of said body, contacting said aortic or said coronary guide device, and retracting back within said body.

47. The method of claim 43, wherein said cone-shaped hollow device is retracted inside said body until reaching a predetermined location, and is capable of protruding out from said body at said predetermined location to create a conical surface area.

48. The method of claim 37, wherein said third elongated instrument is a thoracic catheter having an expandable object and is inserted into said graft at an exterior of said thoracic region of said patient and wherein said thoracic catheter is capable of navigating said graft to said coronary aperture.

49. The method of claim 37, further comprising a coupler at one or both ends of said graft.

50. The method of claim 37, further comprising inserting a fiber optic light/video camera system through said thoracic aperture.

51. The method of claim 37, wherein said aortic catheter passes through said aorta from said thoracic aperture and out of said peripheral artery.

52. The method of claim 37, wherein said aortic catheter is pulled or pushed through a vascular wall via fixation on said aortic guide wire.

53. The method of claim 37, wherein said third elongated instrument is a thoracic catheter having an expandable object, wherein said graft is inserted into said thoracic catheter at an interior of said thoracic region of said patient.

54. The method of claim 37, wherein said graft is within said third elongated instrument.

* * * * *